US008772562B2

(12) United States Patent
Wang et al.

(10) Patent No.: US 8,772,562 B2

(45) Date of Patent: *Jul. 8, 2014

(54) PROCESS FOR MAKING BASESTOCKS FROM RENEWABLE FEEDSTOCKS

(75) Inventors: Kun Wang, Bridgewater, NJ (US); Margaret May-Som Wu, Skillman, NJ (US); Alan Anthony Galuska, Glen Gardner, NJ (US); David Lawrence Stern, Fairfax Station, VA (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 391 days.

This patent is subject to a terminal disclaimer.

(21) Appl. No.: 12/943,131

(22) Filed: Nov. 10, 2010

(65) Prior Publication Data

US 2012/0115762 A1 May 10, 2012

(51) Int. Cl.
*C07C 6/00* (2006.01)
*C07C 6/04* (2006.01)

(52) U.S. Cl.
USPC ........... 585/326; 585/240; 585/638; 585/643; 508/499

(58) Field of Classification Search
USPC ......... 585/240, 250, 252, 256, 254, 314, 324, 585/326, 500, 643, 700, 708, 646
See application file for complete search history.

(56) References Cited

U.S. PATENT DOCUMENTS

| | | | | |
|---|---|---|---|---|
| 4,417,088 | A * | 11/1983 | Miller | 585/533 |
| 4,545,941 | A * | 10/1985 | Rosenburg | 554/163 |
| 5,075,269 | A * | 12/1991 | Degnan et al. | 502/77 |
| 5,444,032 | A * | 8/1995 | Perego et al. | 502/235 |
| 5,451,704 | A * | 9/1995 | Ho et al. | 585/512 |
| 5,961,951 | A * | 10/1999 | Kennedy et al. | 423/708 |
| 6,455,716 | B2 * | 9/2002 | Kenneally et al. | 554/158 |
| 6,723,862 | B2 * | 4/2004 | Shuguang et al. | 554/125 |
| 6,831,184 | B2 | 12/2004 | Zhang et al. | |
| 6,946,567 | B2 | 9/2005 | Zhang et al. | |
| 2001/0044550 | A1 | 11/2001 | Kenneally et al. | |
| 2003/0100780 | A1 | 5/2003 | Zhang et al. | |
| 2003/0191330 | A1 | 10/2003 | Zhang et al. | |
| 2003/0191331 | A1 | 10/2003 | Shuguang et al. | |
| 2005/0154221 | A1 | 7/2005 | Lysenko et al. | |
| 2007/0135663 | A1 | 6/2007 | Aalto et al. | |
| 2007/0161832 | A1 | 7/2007 | Myllyoja et al. | |
| 2008/0027194 | A1 | 1/2008 | Schrodi | |
| 2008/0045731 | A1 * | 2/2008 | Zhang | 554/124 |
| 2008/0132435 | A1 | 6/2008 | Ferreira Fontes et al. | |
| 2009/0029427 | A1 * | 1/2009 | Miller | 435/134 |
| 2009/0229173 | A1 * | 9/2009 | Gosling | 44/308 |
| 2009/0318740 | A1 * | 12/2009 | Guillon et al. | 585/310 |
| 2010/0076236 | A1 * | 3/2010 | Van Heuzen et al. | 585/313 |
| 2010/0160506 | A1 * | 6/2010 | Wu et al. | 524/114 |
| 2010/0187156 | A1 * | 7/2010 | Prentice et al. | 208/60 |

FOREIGN PATENT DOCUMENTS

| | | | |
|---|---|---|---|
| EP | 0130039 | A1 | 2/1985 |
| EP | 1268386 | B1 | 4/2004 |
| EP | 1698686 | | 9/2006 |
| WO | 2008046106 | A | 4/2008 |
| WO | 2008101945 | | 8/2008 |
| WO | 2010074738 | A1 | 7/2010 |

OTHER PUBLICATIONS

Bockisch, Michael (1998). Caproleic acid definition. Fats and Oils Handbook. (pp: p. 61). AOCS Press. Online version available at: http://www.knovel.com/web/portal/browse/display?_EXT_KNOVEL_DISPLAY_bookid=2296&VerticalID=0.*

Shurtleff, W. et al. (2007). Composition of Soy Oil. History of Soybean Crusshing: Soy Oil and Soybean Meal—Part I (pp: p. 5) Soyinfo Center, Lafayette, California.*

Food Chemicals Codex (7th ed). (2010). Oleic Acid Definition. The United States Pharmacopeial Convention. (p. 743) Online version available at: http://www.knovel.com/web/portal/browse/display?_EXT_KNOVEL_DISPLAY_bookid=3812&VerticalID=0.*

Mol, Johannes C. and Regina Buffon, "Metathesis in Oleochemistry", Journal of the Brazilian Chemical Society (1998), 9(1), 1-11.

Mol, J. C., "Application of Olefin Metathesis in Oleochemistry: An Example of Green Chemistry", Green Chemistry (2002), 4(1), 5-13.

Patel, Jim, S. Mujcinovic, W. Roy Jackson, Andrea J. Robinson, Algirdas K. Serelis and Chris Such, "High Conversion and Productive Catalyst Turnovers in Cross-Metathesis Reactions of Natural Oils with 2-Butene", Green Chemistry (2006), 8(5), 450-454.

Johannes C. Mol et al., Metathesis in Oleochemistry, J. Braz. Chem. Soc., Dec. 31, 1998, pp. 1-11, Vo. 9, Soc. Bras. Quimica.

PCT Application No. PCT/US2011/059734, Communicaton from the International Searching Authority, Form PCT/Form PCT/ISA/210, dated Feb. 1, 2013, 4pgs.

* cited by examiner

*Primary Examiner* — Walter D Griffin
*Assistant Examiner* — Jelitza Perez
(74) *Attorney, Agent, or Firm* — Robert A. Migliorini

(57) ABSTRACT

A process for converting feedstock triglycerides to lube basestocks. The process has the steps of (a) metathesizing the feedstock triglycerides with ethylene in the presence of a metathesis catalyst to form alpha olefins and medium-chain triglycerides and (b) hydroisomerizing the medium-chain triglycerides in the presence of a hydroisomerization catalyst and hydrogen to form methyl-branched triglycerides. The alpha olefins may be oligomerized in the presence of an oligomerization catalyst to form poly(alpha olefins).

22 Claims, No Drawings

PROCESS FOR MAKING BASESTOCKS FROM RENEWABLE FEEDSTOCKS

FIELD

The present disclosure relates to a process for making lube basestocks from renewable feedstocks. The present disclosure further relates to relates to a process for converting fatty acids triglycerides into group IV and group V lube basestocks.

BACKGROUND

Lube basestocks are commonly used for the production of lubricants, such as lubricating oils for automobiles, industrial lubricants and lubricating greases. They are also used as process oils, white oils, metal working oils and heat transfer fluids. Finished lubricants consist of two general components, lubricating base oil and additives. Lubricating base oil is the major constituent in these finished lubricants and contributes significantly to the properties of the finished lubricant. In general, a few lubricating base oils are used to manufacture a wide variety of finished lubricants by varying the mixtures of individual lubricating base oils and individual additives.

According to the American Petroleum Institute (API) classifications, lube basestocks are categorized in five groups based on their saturated hydrocarbon content, sulfur level, and viscosity index (Table 1). Lube base oils are typically produced in large scale from non-renewable petroleum sources. Group I, II, and III basestocks are all derived from crude oil via extensive processing, such as solvent extraction, solvent or catalytic dewaxing, and hydroisomerization. Group III base oils can also be produced from synthetic hydrocarbon liquids obtained from natural gas, coal or other fossil resources. Group IV basestocks, the poly(alpha olefins) (PAO), are produced by oligomerization of alpha olefins, such as 1-decene. Group V base oils includes everything that does not belong to Groups I-IV, such as naphthenics, polyalkylene glycols (PAG), and esters.

TABLE 1

| | API classification | | | | |
|---|---|---|---|---|---|
| | Group I | Group II | Group III | Group IV | Group V |
| % Saturates | <90 | ≥90 | ≥90 | Poly | All others |
| % S | >0.03 | ≤0.03 | ≤0.03 | alpha- | not belong- |
| Viscosity | 80-120 | 80-120 | ≥120 | olefins | ing to group |
| Index (VI) | | | | (PAO) | I-IV |

Increasingly, the specifications for finished automotive lubricants require products with excellent low temperature properties, high oxidation stability and low volatility. Generally lubricating base oils are base oils having kinematic viscosity of 3 cSt or greater at 100° C. (Kv100); pour point (PP) of −12° C. or less; and viscosity index (VI) 90 or greater. In general, high performance lubricating base oils should have a Noack volatility no greater than current conventional Group I or Group II light neutral oils. Currently, only a small fraction of the base oils manufactured today are able to meet these demanding specifications.

For environmental, economical, and regulatory reasons, it is of interest to produce fuels, chemicals, and lube oils from renewable sources of biological origin. So far only esters of renewable and biological origin have been used in applications such as refrigeration compressor lubricants, bio-hydraulic oils and metal working oils. In automotive and industrial lubricants, esters from biological sources are used in very small fractions as additives due to technical problems as well as their high prices. For example, ester base oils can hydrolyze readily producing acids, which in turn cause corrosion on lubricating systems.

In contrast, lube basestocks consisting of hydrocarbons from biological sources do not have those technical problems associated with esters from same sources. Most common biological sources for hydrocarbons are natural oils, which can be derived from plant sources such as canola oil, castor oil, sunflower seed oil, rapeseed oil, peanut oil, soy bean oil, and tall oil, or derived from animal fats. The basic structural unit of natural oils and fats is a triglyceride, which is an ester of glycerol with three fatty acid molecules having the structure below:

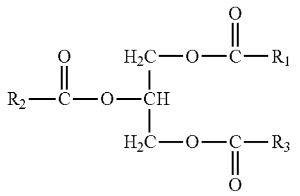

wherein $R_1$, $R_2$, and $R_3$ represent $C_4$-$C_{30}$ hydrocarbon chains. Fatty acids are carboxylic acids containing long linear hydrocarbon chains. Lengths of the hydrocarbon chains most commonly are 18 carbons ($C_{18}$). $C_{18}$ fatty acids are typically bonded to the middle hydroxyl group of glycerol. Typical carbon numbers of the fatty acids linked to the two other hydroxyl groups are even numbers, being between $C_{14}$ and $C_{22}$.

For the purpose of this disclosure, when all the fatty acid chains in a triglyceride have more than 14 carbon atoms, the triglyceride is considered a long-chain fatty acid triglyceride. When one or more of the fatty acid chains in a triglyceride has less than 14 carbon atoms, the triglycerides are considered medium-chain triglycerides.

Fatty acid composition of feedstocks of biological origin may vary considerably depending on the source. While several double bonds may be present in fatty acids, they are non-conjugated (with at least one $—CH_2—$ unit between the double bonds). With respect to configuration, the double bonds of natural fatty acids are mostly of cis form. As the number of the double bonds increase, they are generally located at the free end of the chain. Lengths of hydrocarbon chains and numbers of double bonds depend on the various plant or animal fats or waxes serving as the source of the fatty acid. Animal fats typically contain more saturated fatty acids than unsaturated fatty acids. Fatty acids of fish oil contain high amounts of double bonds, and the average length of the hydrocarbon chains is higher compared to fatty acids of plant oils and animal fats.

Fatty acid triglycerides can also be illustrated by way of example by the following structure:

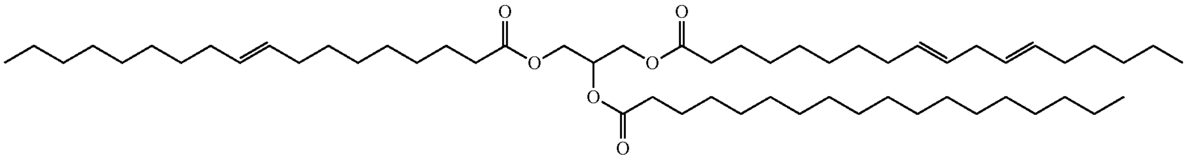 [SMILES: CCCCC/C=C/C/C=C/CCCCCCCC(=O)OCC(COC(=O)CCCCCCC/C=C/CCCCCCCC)OC(=O)CCCCCCCCCCCCCCCCC]

From bottom to top, the fatty acid chains are palmitic, oleic, and linoleic acid. Depending on the source, each of the fatty acid chains can contain between 14 and 22 carbons. Table 2 below provides the fatty acid composition of some common oils from plant and animal sources.

TABLE 2

| | Saturated (%) | Mono-Unsaturated (%) | Poly-Unsaturated (%) |
|---|---|---|---|
| Animal fats | | | |
| Lard | 40.8 | 43.8 | 9.6 |
| Butter | 54.0 | 19.8 | 2.6 |
| Vegetable oils | | | |
| Coconut oil | 85.2 | 6.6 | 1.7 |
| Palm oil | 45.3 | 41.6 | 8.3 |
| Cottonseed oil | 25.5 | 21.3 | 48.1 |
| Wheat germ oil | 18.8 | 15.9 | 60.7 |
| Soya oil | 14.5 | 23.2 | 56.5 |
| Olive oil | 14.0 | 69.7 | 11.2 |
| Corn oil | 12.7 | 24.7 | 57.8 |
| Sunflower oil | 11.9 | 20.2 | 63.0 |
| Safflower oil | 10.2 | 12.6 | 72.1 |
| Rapeseed/ Canola oil | 5.3 | 64.3 | 24.8 |

Metathesis of triglycerides and ethylene is disclosed in U.S. Pat. No. 4,545,941, which is incorporated herein by reference. Alpha-olefins and modified triglycerides are produced. Alpha olefins obtained by the disclosed process can be used in the synthesis of lubricating oils, detergents, plasticizer alcohols, flavors, perfumes, dyes, pharmaceuticals, and resins. Medium-chain triglycerides can be used as dietary components or be converted via hydrolysis to medium-chain fatty acids suitable for a variety of industrial purposes, such as ingredients for soap and "hard butter". Transformation of medium chain triglycerides via hydroisomerization to lubricants is not disclosed in the prior art.

Branched alkyl fatty acids and esters are useful in a number of consumer products including lubricants. Branched fatty acids and alkyl esters that are saturated offer a number of useful features, including better lubricity due to their chain length and random branching, better oxidative stability due to low or no double-bond content, and lower pour point compared to their linear counter-parts. U.S. Pat. No. 6,455,716 discloses a process for the branching of saturated and unsaturated fatty acids and/or alkyl esters thereof by skeletal isomerization over acid/metal bi-functional catalysts.

Currently, group IV lube basestocks (PAO) are manufactured by oligomerizing alpha-olefins from petroleum sources, such as disclosed in U.S. Pat. No. 5,451,704.

With increasing availability of triglycerides it is desirable to take advantage of the renewable feedstocks to produce lube basestocks, thus saving non-renewable petroleum raw materials. There is a need for an integrated process to make both group IV and group V lube basestocks from renewable sources, especially from triglycerides of long-chain fatty acids.

SUMMARY

According to the present disclosure, there is provided a process for converting feedstock triglycerides to lube oils. The process has the steps of (a) metathesizing the feedstock triglycerides with ethylene in the presence of a metathesis catalyst to form alpha olefins and medium-chain triglycerides and (b) hydroisomerizing the medium-chain triglycerides in the presence of a hydroisomerization catalyst and hydrogen to form medium-chain, methyl-branched triglycerides. The alpha olefins may further be oligomerized in the presence of an oligomerization catalyst to form poly(alpha olefins) (PAO).

An embodiment of the reaction sequence is illustrated below:

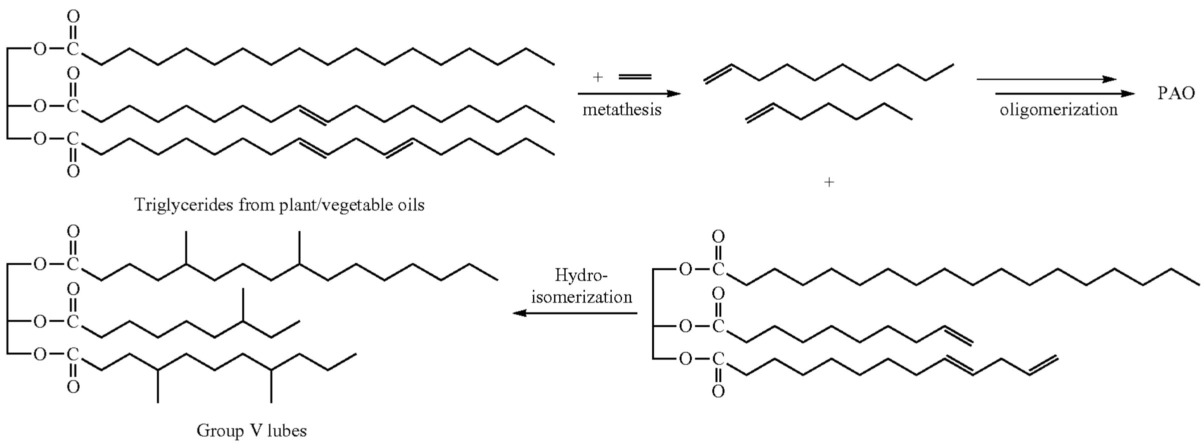

These and other features and attributes of the disclosed processes for converting feedstock triglycerides to lube oils of the present disclosure and their advantageous applications and/or uses will be apparent from the detailed description which follows, particularly when read in conjunction with the figures appended hereto.

DETAILED DESCRIPTION

All numerical values within the detailed description and the claims herein are modified by "about" or "approximately" the indicated value, and take into account experimental error and variations that would be expected by a person having ordinary skill in the art.

The disclosure relates to a process that produces lube basestocks from mixed triglycerides obtainable from natural and/or renewable sources. Natural oils from plants or vegetables take the form of triglycerides of fatty acids. The fatty acid chain can be saturated, mono-unsaturated, or poly-unsaturated. An aspect of the process is the metathesis of the unsaturated fatty acid chains with ethylene resulting in medium chain triglycerides and alpha-olefins including 1-decene. Alpha-olefins can then be converted into PAO-based lube basestocks via technology known in the art. Another aspect of the process is the conversion of the medium chain triglycerides into group V lube basestocks by hydroisomerization. The isomerization and hydrogenation steps can be done either separately or simultaneously.

An embodiment of the reaction sequence is illustrated below:

oils, and fats, oils and waxes obtained by genetic engineering, and mixtures thereof; and g) mixtures thereof.

Advantageous starting natural oils for the processes of the present disclosure should contain a relatively high amount of components having a single double bond in the fatty acid (e.g., mono-unsaturated fatty acids). Examples of the mono-unsaturated fatty acids include cis-5-dodecenoic acid, myristoleic acid (cis-9-tetradecenoic acid, C14:1), palmitoleic (cis-9-hexadecenoic acid, C16:1), oleic acid (cis-9-octadecenoic acid, C18:1), gadoleic acid (cis-11-eicosenoic acid C20:1), erucic acid (cis-13-docosenoic acid C22:1). Although most natural occurring oils contain cis-isomers of fatty acids, their trans-analogs occurred naturally or via isomerization process during treatment, such as hydrogenation, can also be used. Other odd carbon number mono-unsaturated acids, cis or trans form, although rare in natural products, can also be used. Generally, oils rich in the cis-form of the mono-unsaturated acids are most abundant in natural oils especially plant-based oils, and are the preferred feeds. For example, Canola oil, some rapeseed oil or some mustard oil contains 57%-60% monounsaturated fat, olive oil is has 75% monounsaturated fat while tea seed oil commonly contains over 80% monounsaturated fat. Oils that contain some di-unsaturated fatty acid moiety can also be used for the processes disclosed herein. For lube applications, it may be advantageous to use oils with low amount of di-unsaturated fatty acid moiety.

Rapeseed oils, canola oils, mustard oils or olive oils usually are triglycerides of long-chain fatty acid esters. In particular, suitable seed oils for this embodiment may include oils which

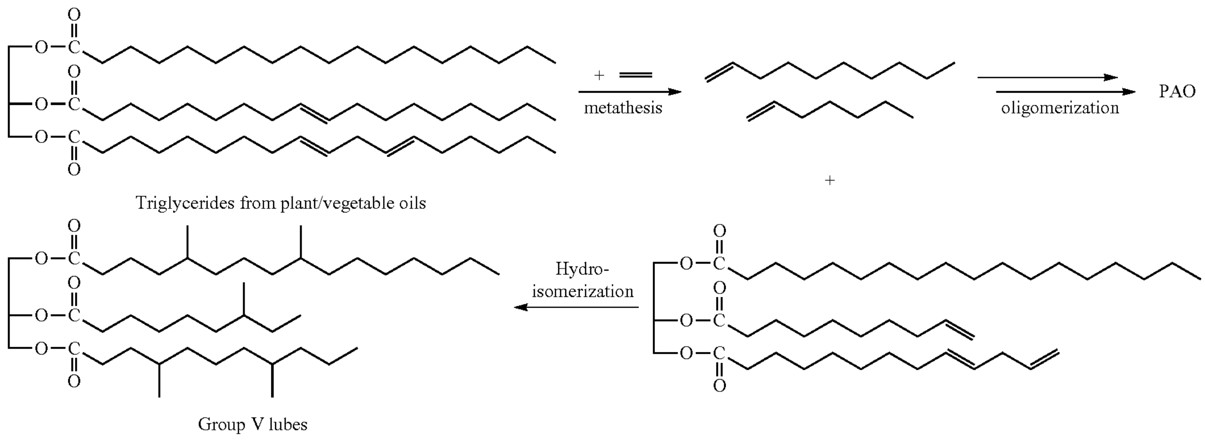

Suitable starting materials of natural or biological origin are selected from the group consisting of: a) plant fats, plant oils, plant waxes; animal fats, animal oils, animal waxes; fish fats, fish oils, fish waxes, and mixtures thereof; and b) free fatty acids or fatty acids obtained by hydrolysis, acid trans-esterification or pyrolysis reactions from plant fats, plant oils, plant waxes, animal fats, animal oils, animal waxes, fish fats, fish oils, fish waxes, and mixtures thereof; and c) esters obtained by transesterification from plant fats, plant oils, plant waxes, animal fats, animal oils, animal waxes, fish fats, fish oils, fish waxes, and mixtures thereof, and d) esters obtained by esterification of free fatty acids of plant, animal and fish origin with alcohols, and mixtures thereof; and e) fatty alcohols obtained as reduction products of fatty acids from plant fats, plant oils, plant waxes, animal fats, animal oils, animal waxes, fish fats, fish oils, fish waxes, and mixtures thereof; and f) waste and recycled food grade fats and have a significant amount of the glycerides of mono-unsaturated acids, such as myristoleic acid, palmitoleic, oleic, gadoleic, behenic, erucic, and lauroleic acids.

In addition to the plant oils or animal fats/oils that can be used for these processes, the fatty acid derivatives from plant oils or animal fats/oils can also be used herein. Examples of the derivatives include mono-esters derived from triglycerides (also known as mono-esters of the fatty acid moieties of the triglycerides). Methods of making such derivatives are known in the art, e.g., see Process Economic Program Report 251 "Biodiesel Production" by Stanford Research Institute (SRI), or U.S. Pat. Nos. 4,303,590; 5,354,878; and 5,525,126 and U.S. Patent Application Publication Nos. 2002/0010359 and 2003/0149289. Further examples of such derivatives include methyl esters of these fatty acids, commonly known as fatty acid methyl ester (FAME) or biodiesel, ethyl esters, propyl esters, and simple fatty acids. In the cases of the derivatives such as the methyl ester or unsaturated fatty acids, they can also be converted into group IV lube basestocks by these transformations: 1) hydrogenation of the fatty acid or esters to yield fatty alcohols; 2) dehydration of the fatty alcohols to make alpha-olefins; 3) oligomerization of the alpha-olefins to making group IV basestocks poly(alpha-olefins).

The metathesis step is carried out in the presence of a catalytically effective amount of a metathesis catalyst. The metathesis reaction is generally catalyzed by a system containing both a transition and a non-transition metal component. The most active and largest number of catalyst systems are derived from the Group VI B transition metals, tungsten and molybdenum. Organoaluminum compounds, and alkyl derivatives of tin, lithium, and magnesium are the most widely used non-transition metal component of a metathesis catalyst system. A preferred catalyst is a tungsten compound and a tin compound. Suitable tungsten compounds include tungsten oxychloride, tungsten pentabromide, tungsten dichloride, tungsten tetrachloride, and tungsten hexachloride. Suitable tin compounds include the alkyl derivatives such as tetramethyl tin and tetra-n-butyl tin. The most preferred metathesis catalyst comprises tungsten hexachloride and tetramethyl tin. To maximize the yields of co-metathesis products, it is preferred that the two catalyst components be present in equimolar amounts and at a concentration of 0.04 to 0.12 moles of each per mole of reactant triglyceride. The catalyst may be supported or unsupported.

Another type of transition metal based metathesis catalyst is organometallic compounds of ruthenium, as disclosed by Grubbs in *Chemical Reviews*, vol. 110(3), pp. 1746-1787 (2010), which is incorporated herein by reference in its entirety.

The metathesis reaction can be carried out neat or in the presence of a solvent. Reaction in the presence of an organic solvent is preferred. The triglycerides are dissolved in the organic solvent. The presence of a solvent improves mixing, and, if added to the triglyceride and partially distilled off before reaction, helps remove traces of water which can poison such metathesis catalysts as tungsten hexachloride. The more commonly used solvents in metathesis reactions include such aliphatic solvents as the saturated hydrocarbons and such aromatic solvents as benzene, chlorobenzene, and toluene. Aliphatic solvents are preferred over the aromatics because of a reduced tendency to interact with the reactants. On the basis of maximizing the yield of co-metathesis products based on a given volume of solvent, preferred solvents are saturated hydrocarbons boiling in the range of 50° C. to 120° C., such as hexane. On a molar basis, the preferred amount of solvent is 0.5 to 5.0 moles per mole triglyceride.

The metathesis reaction is generally carried out at a temperature of 40° C. to 260° C. The reaction does not proceed to a noticeable degree at temperatures below 40° C. The rate of the reactions increases with increasing temperature, but temperatures above 260° C. are undesirable because the triglycerides begin to degrade. The preferred temperature for the metathesis reaction is 50° C. to 120° C.

The metathesis process produces medium-chain triglycerides and alpha-olefins in yields that depend upon the exact conditions employed. Yields of greater than 30 percent are generally attained and yields of greater than 60 percent are attained at preferred conditions. Preferred conditions for the metathesis reaction of a triglyceride and ethylene are as follows: (1) an ethylene partial pressure of 330 psig to 490 psig; (2) a catalyst system of 0.04 to 0.12 moles of tungsten hexachloride and tetramethyl tin per mole triglyceride; (3) a saturated hydrocarbon solvent boiling in the range of 50° C. to 120° C. and present at 0.5 to 5.0 moles per mole triglyceride; (4) a temperature of 50° C. to 120° C.; and (5) a reaction time of greater than 30 minutes. The process can be carried out batch-wise, semi-batch-wise, or continuously.

Additional teachings to metathesis reactions are seen in U.S. Pat. No. 4,545,941, which is incorporated herein by reference in its entirety.

The metathesis reaction can produce a mixture of olefin intermediate co-products, such as propylene, 1-butene, 1-pentene, 1-hexene, 4-methyl-1-pentene, 1-heptene, 1-octene, 1-decene, 1-dodecene, and 1-tetradecene. A preferred olefin product is 1-decene.

Alpha-olefins generated according to the present disclosure can be oligomerized to form poly(alpha-olefins), which can be used as group IV lube basestocks. The olefin oligomerization reaction is carried out at a temperature of −100° C. to 300° C. and preferably −50° C. to 200° C. The reaction is carried out at a pressure is pressure of $10^{-6}$ to 60 atmospheres (bar) (0 to 900 psig) and preferably 0.1 to 10 atmospheres (bar) (1 to 150 psig). The reaction is carried out at a weight hourly space velocity of from 0.1 to 400 and preferably 0.1 to 20.

The olefin oligomerization reaction is carried out in the presence of a catalytically effective amount of a catalyst. Commercially, poly-alpha-olefins (PAO) are manufactured by cationic oligomerization processes employing either boron trifluoride or aluminum trichloride as catalysts. The organic metal halide can be of one or more metal elements selected from Groups IIA, IIB, IIIA, IIIB, IVB, VB, and VIB of the Periodic Table. Suitable organic metal halides include those represented by the formula RMXY, wherein R is an alkyl, alkenyl, or aryl moeity; M is an element selected from Groups IIA, IIB, IIIA, IIIB, IVB, VB, and VIB of the Periodic Table; X is halogen; and Y is selected from the group consisting of halogen, alkyl, alkenyl, aryl, alkoxy, and amido moeities. In one embodiment, R is alkyl, M is a Group IIIA element, e.g., Al, B, or Ga, and Y is selected from the group consisting of halogen, e.g., Cl or Br, and alkyl. A particularly preferred organic metal halide is one wherein RMXY is selected from the group consisting of $EtAlCl_2$, $Me_2AlCl$, $Et_2AlCl$, $Et_2AlCl/EtAlC_2$, and $Et_2AlOMe$, with $EtAlCl_2$ particularly preferred.

The olefin oligomerization reaction can be carried out in a fixed-bed, continuous flow reactor or in a slurry, batch-type operation or continuous stirred tank reactor (CSTR) type operation.

Additional teachings to the olefin oligomerization reaction are seen in U.S. Pat. No. 5,451,704, which is incorporated herein by reference.

The medium-chain fatty acid glycerides obtained from the metathesis step can be further transformed into group V lubes via hydroisomerization under a hydrogen atmosphere using acid/metal bi-functional catalysts. The unsaturated fatty acid chain is saturated by $H_2$ and isomerized to give products with methyl branches. The glyceride ester functionality is not altered during this process. The medium-chain fatty acid glycerides have at least one fatty acid chain having carbon atoms less than 14, more preferably less than 12, and most preferably less than or equal to 10. Additionally, the hydroisomerized products preferably have at least one fatty acid chain with at least one methyl branch.

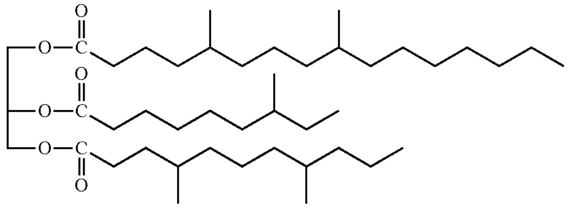 [SMILES: CCCCCCCC(C)CCCC(C)CCCC(=O)OCC(COC(=O)CCC(C)CCCC(C)CCC)OC(=O)CCCCCC(C)CC]

The hydroisomerization reaction is carried out at a temperature of from 240° C. to 380° C., preferably from 280° C. to 350° C., and more preferably from 320° C. to 340° C. The amount of catalyst, preferably a zeolite catalyst containing metal sites is typically from 0.1% to 20%, preferably from 0.5% to 10%, and more preferably from 1% to 6%, by weight of the reaction mixture.

The hydroisomerization reaction is carried out in the presence of hydrogen gas, or in a mixture of gases including hydrogen gas, such as nitrogen, carbon dioxide, argon, and mixtures thereof Hydrogen gas is both generated and consumed in the course of the present reaction, and as such is required to be present in the headspace of the reactor. It is preferable to have a net input of hydrogen gas into the present process during the reaction step in order to bring the reaction to completion. Hydrogen is generated during dehydrogenation of the alkyl chain prior to the isomerization step, then consumed during rehydrogenation of the alkyl chain after the isomerization step is completed. Hydrogen is also consumed if there are any significant levels of unsaturated carbon bonds in the starting feedstock, which are hereby converted into saturates in the course of the isomerization reaction. Certain degree of cracking may occur during isomerization. As a result, monoglycerides and diglycerides with methyl branches on the fatty acid chain may form. Preferably, the total number of carbon in the molecule is greater than 30 for lubricant applications. The mono- and di-glycerides can be removed by distillation or retained in the product if their total carbon number is greater than 30.

The hydroisomerization reaction optionally can be carried out in the presence of a supercritical fluid selected from the group consisting of carbon dioxide, ethene, ethane, propane, and mixtures thereof. The supercritical fluid can speed the overall rate of reaction by greatly increasing the solubility of hydrogen gas into the liquid phase of the reaction.

The hydroisomerization reaction is preferably carried out in a closed system, e.g., in which the reaction pressure is normally less than 1000 pounds per square inch gauge (psig), preferably from 10 to 300 psig, and more preferably 50 to 100 psig. Some pressure is recommended is to prevent vaporization of low boiling substances in the system including those substances contained in the catalyst. Higher pressures are less desirable, in that they are associated with more side reactions, e.g. cracking to alkanes.

The reaction time of hydroisomerization typically takes from 0.1 to 24 hours, preferably from 0.5 to 12 hours, and more preferably from 1 to 6 hours. Since the catalyst tends to be poisoned by coke during the reaction, the reaction normally takes from 1 to 10 hours. If this problem is overcome, the reaction time can be shortened to several minutes or even several seconds. Also, continuous reaction is possible. Excessively long reaction time tends to cause thermal decomposition resulting in decreased yield.

The hydroisomerization reaction can be carried out in a fixed-bed, continuous flow reactor or in a slurry, batch-type operation or continuous stirred tank reactor (CSTR) type operation. The isomerization and hydrogenation steps can be carried out either separately or simultaneously.

The atmosphere in the apparatus (i.e. headspace) is at least 1% hydrogen, preferably from 1% to 100% hydrogen, more preferably from 50% to 100% hydrogen, and still more preferably from 90% to 100% hydrogen.

Useful hydroisomerization catalysts are zeolites that perform hydroisomerization primarily by isomerizing a hydrocarbon feedstock. More preferably, the catalysts are zeolites with a unidimensional pore structure. Suitable catalysts include 10-member ring pore zeolites, such as EU-1, ZSM-35 (or ferrierite), ZSM-11, ZSM-57, NU-87, SAPO-11, and ZSM-22. Preferred materials are EU-2, EU-11, ZBM-30, ZSM-48, or ZSM-23. ZSM-48 is most preferred. Note that a zeolite having the ZSM-23 structure with a silica to alumina ratio of from 20:1 to 40:1 can sometimes be referred to as SSZ-32. Other molecular sieves that are isostructural with the above materials include Theta-1, NU-10, EU-13, KZ-1, and NU-23.

In various embodiments, the catalysts further include a metal hydrogenation component. The metal hydrogenation component is typically a Group VI and/or a Group VIII metal. Preferably, the metal hydrogenation component is a Group VIII noble metal. More preferably, the metal hydrogenation component is Pt, Pd, or a mixture thereof.

The metal hydrogenation component may be added to the catalyst in any convenient manner. One technique for adding the metal hydrogenation component is by incipient wetness. For example, after combining a zeolite and a binder, the combined zeolite and binder can be extruded into catalyst particles. These catalyst particles can then be exposed to a solution containing a suitable metal precursor. Alternatively, metal can be added to the catalyst by ion exchange, where a metal precursor is added to a mixture of zeolite (or zeolite and binder) prior to extrusion.

The amount of metal in the catalyst can be at least 0.1 wt % based on catalyst, or at least 0.15 wt %, or at least 0.2 wt %, or at least 0.25 wt %, or at least 0.3 wt %, or at least 0.5 wt % based on catalyst. The amount of metal in the catalyst can be 5 wt % or less based on catalyst, or 2.5 wt % or less, or 1 wt % or less, or 0.75 wt % or less. For embodiments where the metal is Pt, Pd, another Group VIII noble metal, or a combination thereof, the amount of metal is preferably from 0.1 to 2 wt %, more preferably 0.25 to 1.8 wt %, and even more preferably from 0.4 to 1.5 wt %.

Preferably, the hydroisomerization catalysts have a low ratio of silica to alumina. For example, for ZSM-48, the ratio of silica to alumina in the zeolite can be less than 200:1, or less than 110:1, or less than 100:1, or less than 90:1, or less than 80:1. In preferred embodiments, the ratio of silica to alumina can be from 30:1 to 200:1, 60:1 to 110:1, or 70:1 to 100:1.

The hydroisomerization catalysts can also include a binder. In some embodiments, the hydroisomerization catalysts used in process according to the disclosure are formulated using a low surface area binder, a low surface area binder represents a binder with a surface area of 100 $m^2/g$ or less, or 80 $m^2/g$ or less, or 70 $m^2/g$ or less. Useful metal oxide refractory binders include silica, alumina, titania, zirconia, and silica-alumina.

Alternatively, the binder and the zeolite particle size are selected to provide a catalyst with a desired ratio of micropore surface area to total surface area. In hydroisomerization catalysts, the micropore surface area corresponds to surface area from the unidimensional pores of zeolites in the hydroisomerization catalyst. The total surface corresponds to the micropore surface area plus the external surface area. Any binder used in the catalyst will not contribute to the micropore surface area and will not significantly increase the total surface area of the catalyst. The external surface area represents the balance of the surface area of the total catalyst minus the micropore surface area. Both the binder and zeolite can contribute to the value of the external surface area. Preferably, the ratio of micropore surface area to total surface area for a hydroisomerization catalyst will be equal to or greater than 25%.

A zeolite can be combined with binder in any convenient manner. For example, a bound catalyst can be produced by starting with powders of both the zeolite and binder, combining and mulling the powders with added water to form a mixture, and then extruding the mixture to produce a bound catalyst of a desired size. Extrusion aids can also be used to modify the extrusion flow properties of the zeolite and binder mixture. The amount of framework alumina in the catalyst may range from 0.1 to 2.7 wt %, or 0.2 to 2 wt %, or 0.3 to 1 wt %.

In yet another embodiment, a binder composed of two or more metal oxides can also be used. In such an embodiment, the weight percentage of the low surface area binder is preferably greater than the weight percentage of the higher surface area binder.

Alternatively, if both metal oxides used for forming a mixed metal oxide binder have a sufficiently low surface area, the proportions of each metal oxide in the binder are less important. When two or more metal oxides are used to form a binder, the two metal oxides can be incorporated into the catalyst by any convenient method. For example, one binder can be mixed with the zeolite during formation of the zeolite powder, such as during spray drying. The spray dried zeolite/binder powder can then be mixed with the second metal oxide binder prior to extrusion.

Process conditions in the catalytic hydroisomerization zone include a temperature of from 240 to 420° C., preferably 270 to 400° C., a hydrogen partial pressure of from 1.8 to 34.6 mPa (250 to 5000 psig), preferably 4.8 to 20.8 mPa (700 to 3000 psig), a liquid hourly space velocity of from 0.1 to 10 v/v/hr, preferably 0.5 to 3.0, and a hydrogen circulation rate of from 35 to 1781.5 $m^3/m^3$ (200 to 10000 scf/B), preferably 178 to 890.6 $m^3/m^3$ (1000 to 5000 scf/B).

The metal sites can be incorporated on the surface of the catalyst, within the pores of the catalyst, or both. In a preferred embodiment, the metal sites are incorporated within the pores of the zeolite catalyst. Incorporating the metal within the pores of the zeolite catalyst may be more effective in isomerizing saturated fatty acids and/or alkyl esters into branched molecules as opposed to other types of molecules such as alkanes, substituted aromatics, and oligomers. The percent metal dispersion, as measured by CO chemisorption, is typically from 0.5% to 100% and preferably at least 50%.

Additional teachings to the hydroisomerization catalysts and binders are seen in U.S. Patent Publication No. 2010/0187156 A1, which is incorporated herein by reference.

Additional teachings to the hydroisomerization reaction are seen in U.S. Pat. No. 6,455,716 B2, which is incorporated herein by reference.

Two types of lube basestocks are generated from the process of this disclosure, namely group IV (PAO) and group V (triglycerides of medium chain fatty acids with methyl branches). The lube basestocks can exhibit a viscosity index of at least 100 and preferably at least 110, as determined by the method of ASTM D 2270. The viscosity index of the product may be as high as 120 or higher.

Depending on the degree of oligomerization for alpha-olefins controlled by the selection of catalyst, reaction temperature, residence time, the poly(alpha-olefins) group IV basestocks can have a 100° C. viscosity of 2.5 cSt to 100 cSt, most preferably 2.5 cSt to 10 cSt, or alternatively 3 cSt to 10 cSt, or alternatively 3 cSt to 20 cSt, or alternatively 3 cSt to 50 cSt, or alternatively 4 cSt to 10 cSt, or alternatively 4 cSt to 20 cSt, or alternatively 4 cSt to 8 cSt, or alternatively 15 cSt to 100 cSt, or alternatively 20 cSt to 80 cSt. For the low viscosity range product, the width or distribution of the carbon number range is no more than 10 carbons, preferably no more than 9 carbons, and particularly preferably no more than 4 carbons (determined by field ionization mass spectrometry, FIMS). More than 50%, preferably more than 75% and particularly preferably more than 80% by weight of the base oil contains hydrocarbons belonging to this narrow carbon number distribution.

The group V basestocks containing medium chain fatty acid glycerides have at least one fatty acid chain having carbon atoms less than 14, more preferably less than 12, and most preferably less or equal to 10. Additionally, the hydroisomerized products, i.e., methyl-branched glycerides, have at least one fatty acid chain with at least one methyl branch.

The group V basestocks containing medium chain fatty acid glycerides can be used as group V lube basestocks, which can have a 100° C. viscosity of 2.5 cSt to 100 cSt, most preferably 2.5 cSt to 10 cSt, or alternatively 3 cSt to 10 cSt, or alternatively 3 cSt to 20 cSt, or alternatively 3 cSt to 50 cSt, or alternatively 4 cSt to 10 cSt, or alternatively 4 cSt to 20 cSt, or alternatively 4 cSt to 8 cSt, or alternatively 15 cSt to 100 cSt, or alternatively 20 cSt to 80 cSt. For the low viscosity range product, the width or distribution of the carbon number range is no more than 10 carbons, preferably no more than 9 carbons, and particularly preferably no more than 4 carbons (determined by field ionization mass spectrometry, FIMS). More than 50%, preferably more than 75% and particularly preferably more than 80% by weight of the base oil contains hydrocarbons belonging to this narrow carbon number distribution.

Sulfur content of the basestocks is preferably less than 300 ppm, preferably less than 50 ppm, and particularly preferably less than 1 ppm (as measured by ASTM D 3120). Nitrogen content of the base oil of the disclosure is less than 100 ppm, preferably less than 10 ppm, and particularly preferably less than 1 ppm (as measured by ASTM D4629).

Volatility of the basestocks with a narrow boiling range, obtained according to the disclosure and measured according to Noack Volatility method (or ASTM D5800 method), is extremely low compared to similar products of the prior art. The product Noack volatility can range from less than 5 wt % for a 20 cSt and higher viscosity product to less than 50 wt % for a fluid of 2.5 cSt. For a fluid of 3 to 8 cSt, the volatility typically can range from 3% to 25%. For fluid of 3.5 to 6 cSt, the volatility can range from 4% to 15% depending on fluid viscosity.

The pour point of the basestocks is usually much lower than conventional Group I to Group III base stock obtained from direct petroleum processing. Depending on viscosity, the new basestocks will have pour point less than −15° C., preferably less than −20° C., preferably less than −30° C., preferably less than −40° C. Accordingly, the base stock is very suitable for demanding low temperature conditions.

The properties of the basestocks provide excellent performance, including very narrow carbon number ranges and distillation ranges. The PAO generated according to the process of this disclosure provides saturated hydrocarbons exhibiting superior viscosity properties and excellent low temperature properties. Hydroisomerization of the medium chain triglyceride imparts improved oxidative stability and maintains excellent low temperature properties for the lube basestocks. The base stock is well suited as base oils without blending limitations. The base stock is also compatible with lubricant additives. The base stock can optionally be blended with other basestocks to form lubricants. Useful co-base lube stocks include Group I-V oils and gas-to-liquid (GTL) oils.

Lubricants incorporating the saturated hydrocarbons may optionally include lube base oil additives, such as detergents, dispersants, antioxidants, anti-wear additives, pour point depressants, viscosity index modifiers, friction modifiers, defoaming agents, corrosion inhibitors, wetting agents, rust inhibitors, and the like. The additives are incorporated with the saturated hydrocarbons to make a finished lubricant that has desired viscosity and physical properties. Typical additives used in lubricant formulation can be found in the book "Lubricant Additives, Chemistry and Applications", Ed. L. R. Rudnick, Marcel Dekker, Inc. 270 Madison Ave. New York, N.J. 10016, 2003.

The base stock can be employed in a variety of lubricant-related end uses, such as a lubricant oil or grease for a device or apparatus requiring lubrication of moving and/or interacting mechanical parts, components, or surfaces. Useful apparatuses include engines and machines. The base stock is most suitable for use in the formulation of automotive crank case lubricants, automotive gear oils, transmission oils, many industrial lubricants including circulation lubricant, industrial gear lubricants, grease, compressor oil, pump oils, refrigeration lubricants, hydraulic lubricants, metal working fluids. Furthermore, the base stock is derived from natural or renewable sources.

Applicants have attempted to disclose all embodiments and applications of the disclosed subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All patents, test procedures, and other documents cited herein, including priority documents, are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

What is claimed is:

1. A process for converting feedstock long chain fatty acid glycerides to lube basestocks, comprising:

(a) metathesizing the feedstock long-chain fatty acid glycerides with ethylene in the presence of a metathesis catalyst to form alpha olefins and medium-chain glycerides, (b) hydroisomerizing the medium-chain glycerides in the presence of a hydroisomerization catalyst and hydrogen to form methyl-branched glycerides, and (c) oligomerizing the alpha olefins in the presence of an oligomerization catalyst to form poly(alpha olefins).

2. The process of claim 1, wherein the reaction between the feedstock long-chain fatty acid glycerides and the ethylene is carried out at a temperature of from 40° C. to 260° C.

3. The process of claim 1, wherein the metathesis catalyst is a catalyst system having a transition metal component and a non-transition metal component.

4. The process of claim 3, wherein the transition metal component is selected from the group consisting of tungsten compound, a molybdenum compound, and a ruthenium compound; and wherein the non-transition metal component is selected from the group consisting of a tin compound, a lithium compound, and a magnesium compound.

5. The process of claim 1, wherein the oligomerization is carried out at a temperature of from −100° C. to 300° C.

6. The process of claim 1, wherein the oligomerization catalyst is selected from the group consisting of aluminum compounds and boron compounds.

7. The process of claim 1, wherein the hydroisomerizing is carried out at a temperature of from 240° C. to 380° C.

8. The process of claim 1, wherein the hydroisomerization catalyst is selected from the group consisting of iron, cobalt, nickel, ruthenium, rhodium, palladium, osmium, iridium, and platinum, and wherein the catalyst is on a solid support.

9. The process of claim 8, wherein the hydroisomerization catalyst is platinum.

10. The process of claim 8, wherein the hydroisomerization catalyst includes a molecular sieve having a $SiO_2$:$Al_2O_3$ ratio of 200:1 to 30:1 and from 0.1 wt % to 2.7 wt % framework $Al_2O_3$ content.

11. The process of claim 10, wherein the molecular sieve is selected from the group consisting of EU-1, ZSM-35, ZSM-11, ZSM-57, NU-87, ZSM-22, EU-2, EU-11, ZBM-30, ZS-48, ZSM-23, and a combination thereof.

12. The process of claim 11, wherein the molecular sieve is ZSM-48.

13. The process of claim 8, wherein the hydroisomerization catalyst further comprises a metal oxide refractory binder having a surface area of 100 $m^2$/g or less.

14. The process of claim 13, wherein the hydroisomerization catalyst exhibits a micropore surface area to total surface area of greater than or equal to 25%, wherein the total surface area equals the surface area of the external zeolite plus the surface area of the metal oxide refractory hinder.

15. The process of claim 13, wherein the metal oxide refractory binder is selected from the group consisting of silica, alumina, titania, zirconia, and silica-alumina.

16. The process of claim 13, further comprising a second metal oxide refractory binder different from the first metal oxide refractory binder.

17. The process of claim 16, wherein the second metal oxide refractory binder is selected from the group consisting of silica, alumina, titanic, zirconia, and silica-alumina.

18. The process of claim 1, wherein the hydroisomerization catalyst includes from 0.1 to 5 wt % platinum.

19. The process of claim 1, wherein the alpha olefins include 1-decene and 1-heptene.

20. The process of claim 1, wherein the feedstock glycerides have fatty acid chains each containing 10 to 40 carbon atoms.

21. The process of claim 1, wherein the medium-chain glycerides have at least one fatty acid chain with less than 14 carbon atoms.

22. The process of claim 1, wherein the feedstock glycerides are obtained from renewable or natural sources.

* * * * *